United States Patent [19]

Stoakley et al.

[11] Patent Number: 4,864,865
[45] Date of Patent: Sep. 12, 1989

[54] TENSILE FILM CLAMPS AND MOUNTING BLOCK FOR THE RHEOVIBRON AND AUTOVIBRON VISCOELASTOMETER

[75] Inventors: Diane M. Stoakley; Anne K. St. Clair, both of Poquoson; Bruce D. Little, Grafton, all of Va.

[73] Assignee: The United States of America as represented by the Administrator of the National Aeronautics and Space Administration, Washington, D.C.

[21] Appl. No.: 267,146

[22] Filed: Nov. 4, 1988

[51] Int. Cl.⁴ .............................................. G01N 3/04
[52] U.S. Cl. ........................................ 73/831; 73/860
[58] Field of Search ................. 73/860, 856, 857, 859, 73/159, 831

[56] References Cited

U.S. PATENT DOCUMENTS 4,231,248 11/1980 Rolinski et al. .................. 73/856 X
4,721,000 1/1988 Scanlon .......................... 73/860 X Primary Examiner—Jerry W. Myracle
Attorney, Agent, or Firm—George F. Helfrich; John R. Manning; Charles E. B. Glenn

[57] ABSTRACT

A set of film clamps and a mounting block for use in the determination of tensile modulus and damping properties of films in a manually operated or automated Rheovibron. These clamps and mounting block provide uniformity of sample gripping and alignment in the instrument. Operator dependence and data variability are greatly reduced.

4 Claims, 3 Drawing Sheets

TENSILE FILM CLAMPS AND MOUNTING BLOCK FOR THE RHEOVIBRON AND AUTOVIBRON VISCOELASTOMETER

ORIGIN OF THE INVENTION

The invention described herein was made by employees of the United States Government and may be manufactured and used by or for the Government for governmental purposes without the payment of any royalties thereon or therefor.

BACKGROUND OF THE INVENTION

1. Field of the Invention

This invention relates generally to materials characterization. It relates in particular to the reproducible and uniform gripping of a film sample to be tested on the Rheovibron and Autovibron Viscoelastometer.

2. Description of Related Art

The Rheovibron Viscoelastometer (Toyo Measuring Instruments) has been used for many years for measuring the dynamic mechanical properties of polymers. See M. Takayanagi, "Viscoelastic Properties of Crystalline Polymers," *Mem. Fac. Eng. Kyushu Univ.*, 23, 1 (1963). This instrument measures the temperature dependence of the complex modulus ($E^*$) and loss tangent (tan $\delta$) of viscoelastic materials at specific frequencies. A small amplitude sinusoidal tensile strain is imposed on one end of a clamped file sample and the sinusoidal tensile stress is measured at the other end. When operated manually the instrument is very labor intensive, requiring the constant attention of the operator for hours at a time if a wide temperature range is covered. In addition, sample mounting, maintaining sample tension, and maintaining sufficiently small intervals between data points are all operator dependent.

The Autovibron DDV-II-C (automated Rheovibron) was introduced by IMASS, Inc., in an effort to overcome many of these problems. See IMASS, Inc., Product Bulletin, Accord, Mass. (1980). This system provides increased sensitivity of measurement, constant tension on the film sample, automatic data logging, and short temperature intervals between successive measurements. These improvements are accomplished with the use of a multiprogrammer, programmable calculator and lock-in analyzer. In spite of the many advantages offered by the automated system, a problem still exists in achieving reproducible film clamping. The sample clamps or chucks provided with both the manual and automated systems for tensile measurements are "alligator clamps" illustrated in FIG. 1. The spring 11 on these clamps is depressed, opening the jaws 12 for film mounting, then released to allow the clamps to grip the film 13. The spring is fatigued over time with continued temperature cycling, making it difficult to reproducibly grip the samples. In addition, the gripping jaws of some of the clamps are not uniformly parallel, causing a pinching of the film in spots and little contact in others. Finally, perfecting the film alignment is limited by the necessity of positioning the film in clamps that are already in the instrument, thereby limiting operator visibility and maneuverability while causing unnecessary agitation to the transducer. Data obtained on the Rheovibron DDV-II-C (manual or automated) can show large variations between runs (on the order of 30 to 50%), due in large part to sample misalignment and yielding or slippage of the sample in the clamps. See D. J. Massa, J. R. Flick and S. E. B. Petrie, *ACS Coat. and Plast. Prep.*, 35, 371 (1975), as well as A. R. Wedgewood and J. C. Seferis, *Polymer*, 22, 966 (1981).

In an effort to alleviate these problems, various new clamps were designed by prior art for testing polymers on the Rheovibron in tension in addition to clamps designed for shear and compression modes. See D. J. Massa, et al., supra, as well as T. Murayama, *J. Appl. Polym. Sci.*, 20, 2593 (1976).

Although these new tensile clamps offer some improvements in clamping reproducibility over the alligator clamps, they require horizontal rather than vertical mounting of the films, and still remain operator dependent to assure proper film alignment.

The Massa, et al design 14 (see D. J. Massa, et al., supra) improves the clamp design by eliminating the spring clamping, replacing it with an Allen screw 15 and an alignment pin 16 to position the top portion of the clamp and hold the film (see FIG. 2). This design, however, still requires positioning the film and securing it while the clamps are mounted in the instrument. The side view of this horizontally clamped film is obstructed by the Rheovibron heating block, preventing an easy check of uniform gripping. Film alignment and uniform gripping in the holder are not assured, as the film can easily be aligned slightly off the clamp axis, whether through operator error or because of a slight torque imposed on the film in tightening the Allen screw.

The Wedgewood, et al clamps 17 (see S. R. Wedgewood, et al, supra) provide a definite advantage over the previous clamps in being able to mount and align a film sample 13 away from the instrument (see FIG. 3). As with the Massa design (FIG. 2) however, this design requires horizontal mounting, with the side (edge on) view of the film obstructed by the heating block. Holding the small clamps stationary while mounting the film is also awkward. More importantly, however, the circular design still allows for alignment of the clamp slightly off axes in the clamp holder.

SUMMARY OF THE INVENTION

It is the primary object of the present invention to obviate the difficulties and disadvantages inherent in the prior art by providing a set of film clamps and a mounting block useful in determining tensile modulus and damping properties of films in a manually operated Rheovibron Viscoelastometer or an automated Rheovibron Viscoelastometer (Autovibron), which film clamps and mounting block provide uniformity of sample gripping and alignment in the testing instrument, thereby reducing operator dependence and data variability.

According to the present invention, clamps allow for sample mounting in T-clamps on a film mounting fixture that is removed from a Rheovibron or an Autovibron. A mounting fixture securely holds the T-clamps and assures alignment and reproducible positioning of a film in these clamps. The film specimen is placed on the mounting fixture and is aligned by positioning the edge of the film along a ledge that is spaced so that a film of specified width will be centered on the T-clamps. The bottoms of the T-clamps fit into cut outs in the mounting block and are securely locked into place, assuring reproducible positioning. The top portions of the T-clamps fit over two alignment pins and are secured to the bottom of the clamps by an Allen screw. To assure that the film does not slip and is not twisted or unevenly clamped as the top of a T-clamp is tightened, a rectangular film holder is placed over the film. This holder is held in position by screwing a top plate, which extends over the film holder, to the mounting block.

After both ends of the film are secured in the T-clamps, the top plate and film holder are removed. The film may then be viewed from the side to assure the operator that the clamping in uniform.

Set screws on the side of the mounting fixture are then loosened and the clamped film and T-clamps may be removed from the block. The T-clamps are then mounted in the Rheovibron or Autovibron in U-clamps. The U-clamps are on rods that are connected to the stress and strain gauges of the instrument. This portion of the clamping assembly is left in place at all times. The T-clamps are slipped into the U-clamps so that a T-clamp runner fits into a U-clamp groove, assuring reproducible and on-axis alignment of the film. An Allen head set screw on the top side of the clamps eliminates slippage of the T-clamps during film tensioning and data acquisitions. This gripping assembly results in a vertical film mounting, allowing an edge on view of the film as a final check on sample mounting.

BRIEF DESCRIPTION OF THE DRAWINGS

For a complete understanding of the present invention, including its primary object and attending benefits, reference should be made to the Description of the Preferred Embodiments below. This Description should be read together with the accompanying drawings, wherein.

DESCRIPTION OF THE PREFERRED EMBODIMENT

Figure 1:
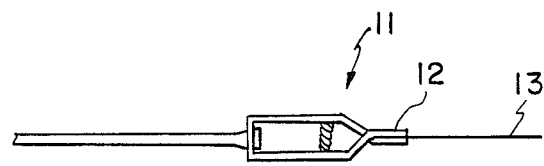
FIG. 1 is a schematic view of "alligator clamps"—a clamping device of the prior art—a discussion of which is found in the Description of Related Art, above.
Figure 2:
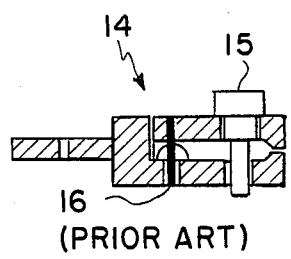
FIG. 2 is a schematic view of another clamping device of the prior art—the Massa design—a discussion of which is also found in the Description of Related Art, above.
Figure 3:
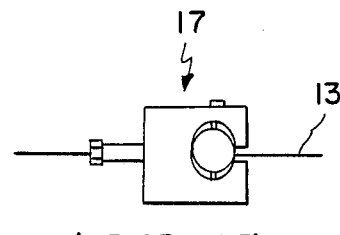
FIG. 3 is a schematic view of yet another clamping device of the prior art—the Wedgewood design—a discussion of which is also found in the Description of Related Art, above.
Figure 4:
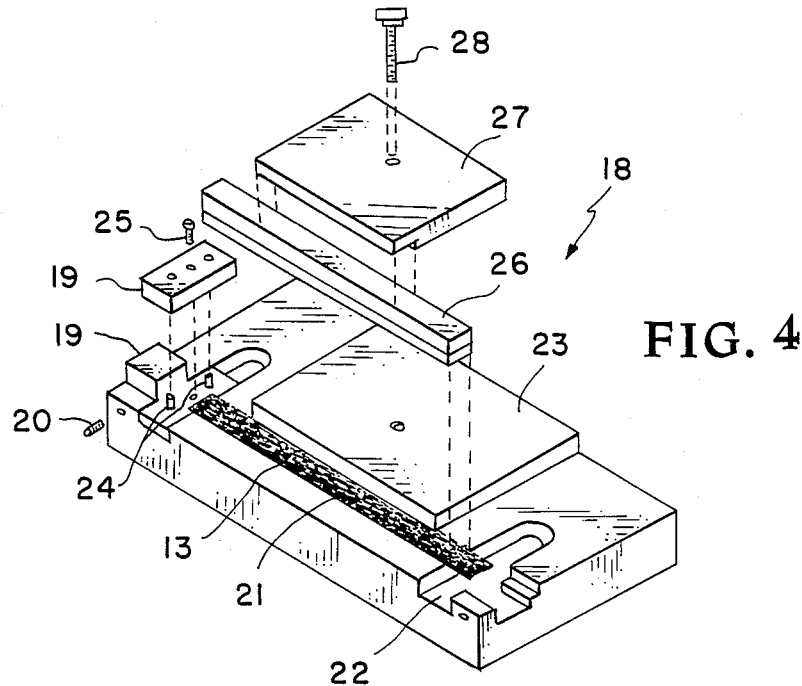
FIG. 4 is a schematic view of a film block and T-clamps according to the present invention.

Referring now to FIG. 4, a mounting fixture 18 is shown which allows for the mounting of a film sample 13 in T-clamps 19. Mounting fixture 18 securely holds T-clamps 19 by means of set screws 20, assuring alignment and reproducible positioning of film 13 in these clamps. Film specimen 13 is placed on mounting fixture 18, and is aligned by positioning the leading edge of the film along ledge 21, which is spaced so that a film of specified width will be centered on the T-clamps. The bottom of each T-clamp 19 fits into a cut out 22 in mounting block 23, and is securely locked place therein by means of set screw 20, assuring reproducible positioning. The top portion of each T-clamp fits over alignment pins 24, which are carried by the bottom portion of each T-clamp, and the top and bottom portions of each T-clamp are joined securely by means of Allen screw 25. In order to ensure that film 13 is not twisted or unevenly clamped as the top of each T-clamp 19 is tightened down, rectangular film holder 26 is placed over film 13 and is held in position thereover by means of top plate 27, which extends over film holder 26 to mounting block 23, and is secured by means of bolt 28.

Figure 5:
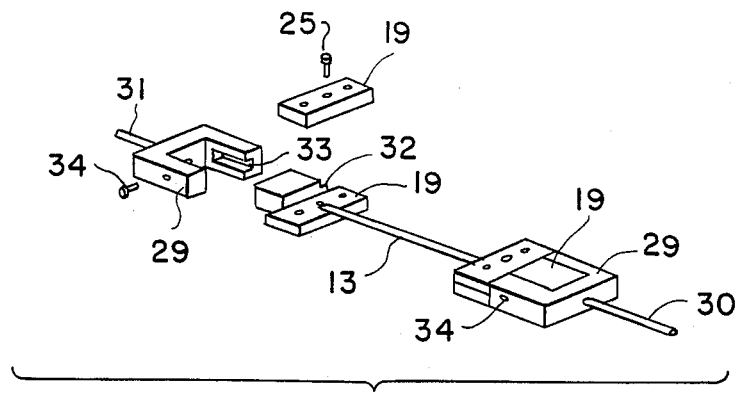
FIG. 5 is a schematic view of Rheovibron U-clamps and T-clamps according to the present invention.

After both sides of film 13 have been secured in T-clamps 19, top plate 27 and film holder 26 are removed. Film 13 may then be viewed from the side to assure the operator that the clamping has been accomplished uniformly. Set screws 20 are then loosened in the side of mounting fixture 18, and T-clamps 19 are removed from mounting block 23 along with film 13. T-clamps 19 are then mounted in U-clamps 29 of the Autovibron or Rheovibron instrument, as seen in FIG. 5. The U-clamps 29 are fastened to rods 30 and 31, which are connected to stress and strain gauges of the instrument. T-clamps 19 are inserted into U-clamps 29 so that T-clamp runner 32 fits into U-clamp groove 33, ensuring reproducible and on-axis alignment of film 13.

Allen head set screws 34 eliminate any slippage of T-clamps 19 during film tensioning and data acquisition. Such a gripping assembly results in a vertical film mounting, allowing an edge-on view of the film as a final check on sample mounting.

EXAMPLES

Example 1

DuPont Kapton ® H-film, 0.0050 cm thick, was cut in a strip 0.40 cm wide. This film sample was mounted according to the present invention as described above in the T-clamps using the mounting block, and was then placed in an Autovibron in the U-clamps. The modulus of the film was determined at four frequencies at room temperature.

| Frequency (Hz) | Modulus $\times 10^{10} \frac{\text{dynes}}{\text{cm}^2}$ |
|---|---|
| 3.5 | 3.059 |
| 11.0 | 3.069 |
| 35.0 | 3.107 |
| 110.0 | 3.255 |

A linear regression of this data (correlation coefficient of 0.999) gives a modulus at 0 frequency of $3.048 \times 10^{10}$ dynes/cm$^2$. E. I. Dupont de Nemours Company, Inc. literature ("Kapton ® Polyimide Film, Summary of Properties", p. 4 (1983)) gives a room temperature tensile modulus for Kapton ® film of 430,000 psi, which is equivalent to $2.97 \times 10^{10}$ dynes/cm$^2$. The literature value and the value obtained experimentally herein differ by 2.6%.

Example 2

A polyimide film was prepared from a polyamic acid resin of 3,3'4,4'-benzophenone tetracarboxylic acid dianhydride (BTDA) and 4,4'-oxydianiline (ODA), 15 weight percent solids in N,N-dimethylacetamide (DMAc). The polyamid acid film was imidized by heating to 300° C. The resulting 0.0025 cm thick film was cut for Rheovibron testing (0.40 cm wide) and Instron testing (2.54 cm wide) for determination of tensile modulus. Using the clamps of this invention, the modulus was determined on the Autovibron at four frequencies.

| Frequency (Hz) | Modulus × $10^{10}$ $\frac{dynes}{cm^2}$ |
|---|---|
| 3.5 | 3.187 |
| 11.0 | 3.215 |
| 35.0 | 3.259 |
| 110.0 | 3.417 |

A linear regression of this data (correlation coefficient of 0.0999) gives a tensile modulus at 0 frequency of $3.185 \times 10^{10}$ dynes/cm$^2$. Instron data was determined using a three-inch gage length and a cross-head speed of 0.2 in/min on ten film strips. The average tensile modulus of the BTDA/ODA film as determined by Instron was 448,000 psi or $3.090 \times 10^{10}$ dynes/cm$^2$. These values as determined experimentally by Autovibron and Instron differed by 3.0%.

Example 3

Kapton® H film, 0.0050 cm thick, was run four separate times using the clamps of this invention on an Autovibron. The room temperature modulus and tan δ values are shown below for the separate runs at 11 Hz.

| Run # | Modulus | Tan δ |
|---|---|---|
| 1 | 3.063 | 0.008 |
| 2 | 3.044 | 0.008 |
| 3 | 3.039 | 0.009 |
| 4 | 3.052 | 0.008 |
| Average | 3.050 | 0.008 |

The percent deviation from the mean averaged 0.3% for the modulus.

Kapton® H film run on the Autovibron using the standard alligator claps supplied with the instrument gave room temperature modulus and tangent δ values at 11 Hz as shown below.

| Run # | Modulus | Tan δ |
|---|---|---|
| 1 | 3.708 | 0.012 |
| 2 | 3.953 | 0.014 |
| 3 | 3.169 | 0.009 |
| 4 | 3.582 | 0.015 |
| Average | 3.603 | 0.013 |

The percent deviation from the mean average 6.3% for the modulus with less consistency in the tan δ also.

Example 4

Figure 6:
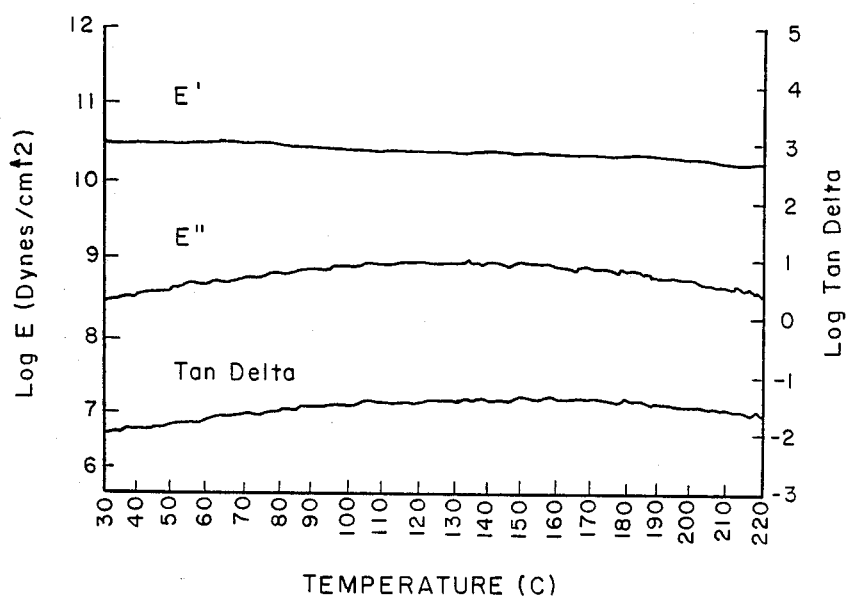
FIG. 6 is a plot of E and Tan δ vs. temperatures obtained from an Autovibron test run on Kapton ® H film using alligator clamps supplied with the instrument.
Figure 7:
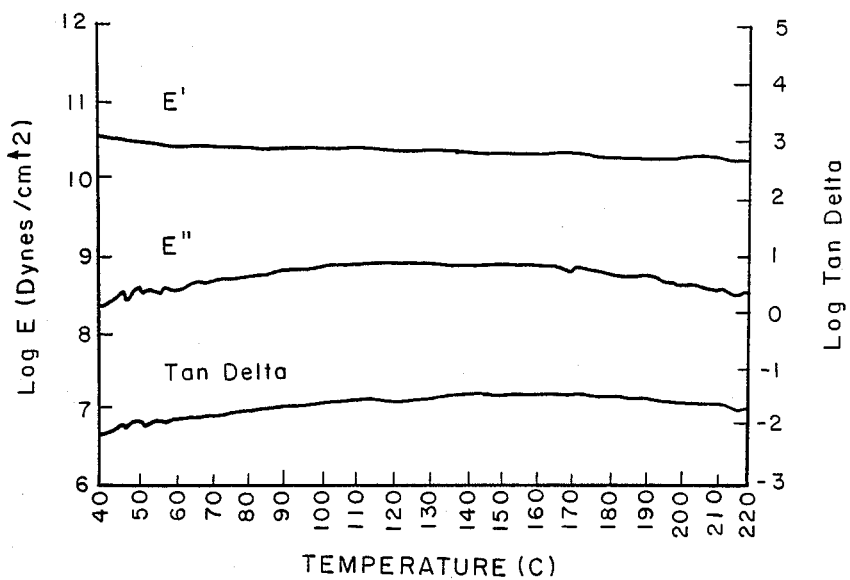
FIG. 7 is a plot of E and Tan δ vs. temperature obtained from an Autovibron test run on Kapton ® H film using film clamps according to the present invention.

BTDA/ODA polyimide film was run four times each from room temperature to 220° C. using alligator clamps and the clamps of this invention. A representative plot of data obtained with the alligator clamps is shown in FIG. 6, and a representative plot of data obtained with clamps according to the present invention is shown in FIG. 7. The data forming these two plots is essentially the same. However, the modulus data variability among the four elevated temperature runs was ±9-12% using the alligator clamps, and only ±3-4% using the clamps of this invention.

Example 5

Figure 8:
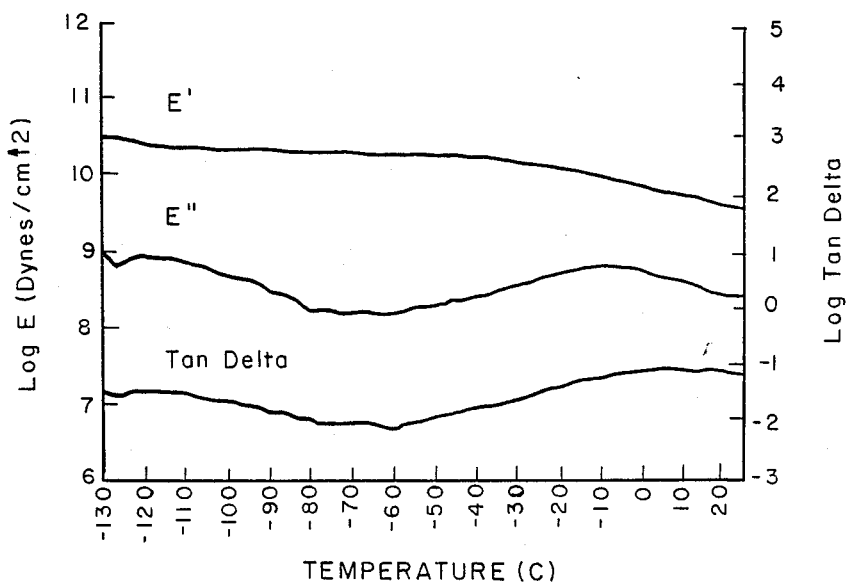
FIG. 8 is a plot of E and Tan δ vs. temperature obtained from an Autovibron test run on polyethylene film using film clamps according to the present invention at temperatures below room temperature.

The clamps of this invention were tested below room temperature by running polyethylene film from −130° C. to 20° C. A sample run is shown in FIG. 8. Another sample of this film was run to determine low temperature reproducibility. Results are tabled below.

| Run # | Modulus, $\frac{dynes}{cm^2}$ | Temperature (°C.) |
|---|---|---|
| 1 | $2.280 \times 10^{10}$ | −100 |
| 2 | $2.136 \times 10^{10}$ | −100 |
| 1 | $1.764 \times 10^{10}$ | −50 |
| 2 | $1.678 \times 10^{10}$ | −50 |
| 1 | $7.377 \times 10^9$ | 0 |
| 2 | $7.086 \times 10^9$ | 0 |

These values differ from the average by 2–3%.

Although the present invention has been described in detail with respect to certain preferred embodiments thereof, it is understood by those of skill in the art that variations and modifications in this detail may be effected without any departure from the spirit and scope of the present invention, as defined in the hereto-appended claims.

What is claimed is:

1. A device for mounting a film sample for viscoelastomeric testing, which device comprises:
   an elongated mounting block having two cut out areas therein, one at each end thereof, each cut out area being adapted to receive and securely fasten a mounting clamp therein;
   two mounting clamps, each having a quadrangular top member and a T-shaped bottom member adapted to be received by and securely fastened within one of said cut out areas, each bottom member having a plurality of alignment pins projecting perpendicularly from the top surface thereof for engagement with a plurality of holes in a top member for precise location and fastening of said top and bottom members after an end of a film sample has been exactly positioned therebetween, said top and bottom members having means for the secure fastening thereof, the mounting clamps being adapted to be received and securely fastened within fastening appliances employed in viscoelastomeric testing;
   film alignment means located on the mounting block to facilitate the exact positioning of each end of the film sample within top and bottom members of each mounting clamp; and
   means for preventing contorting of the film sample while top and bottom members of each mounting clamp are being securely fastened.

2. The device of claim 1, wherein the fastening appliances employed in viscoelastomeric testing are U-clamps of the Rheovibron/Autovibron.

3. The device of claim 2, wherein the film alignment means is a ledge extending along the length of the mounting block in the direction of the two cut out areas.

4. The device of claim 2, wherein the means for preventing contorting of the film sample comprises a rectangular film holder which is placed over the film sample and held in position thereover by means of a top plate extending over the film holder to the mounting block, to which it is secured.

\* \* \* \* \*